(12) United States Patent
Lo et al.

(10) Patent No.: US 8,860,793 B2
(45) Date of Patent: Oct. 14, 2014

(54) CAMERA SYSTEM WITH AUTONOMOUS MINIATURE CAMERA AND LIGHT SOURCE ASSEMBLY AND METHOD FOR IMAGE ENHANCEMENT

(75) Inventors: Yu-Hwa Lo, San Diego, CA (US); Yoav Mintz, San Diego, CA (US); Truong Nguyen, San Diego, CA (US); Jack Tzeng, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 782 days.

(21) Appl. No.: 13/124,659

(22) PCT Filed: Oct. 15, 2009

(86) PCT No.: PCT/US2009/060745
§ 371 (c)(1),
(2), (4) Date: Jul. 8, 2011

(87) PCT Pub. No.: WO2010/045406
PCT Pub. Date: Apr. 22, 2010

(65) Prior Publication Data
US 2011/0261178 A1    Oct. 27, 2011

Related U.S. Application Data

(60) Provisional application No. 61/105,542, filed on Oct. 15, 2008.

(51) Int. Cl.
| H04N 7/18 | (2006.01) |
| A61B 1/06 | (2006.01) |
| A61B 19/00 | (2006.01) |
| G03B 15/05 | (2006.01) |
| A61B 1/05 | (2006.01) |

(52) U.S. Cl.
CPC .............. *A61B 1/05* (2013.01); *A61B 1/0676* (2013.01); *A61B 19/5212* (2013.01); *A61B 1/0684* (2013.01); *G03B 15/05* (2013.01); *A61B 2019/521* (2013.01)
USPC .......................................................... 348/68

(58) Field of Classification Search
CPC .................................................... H04N 5/232
See application file for complete search history.

(56) References Cited

U.S. PATENT DOCUMENTS

| 4,890,903 A | 1/1990 | Treisman et al. |
| 5,233,470 A | 8/1993 | Wu |

(Continued)

FOREIGN PATENT DOCUMENTS

| GB | 2184562 A | 6/1987 |
| JP | 2002169005 A | 6/2002 |
| WO | 0058763 A1 | 10/2000 |

OTHER PUBLICATIONS

Villasenor et al. ("Wavelet Filter Evaluation for Image Compression" IEEE Trans. on Image Processing, vol. 4, No. 8, Aug. 1995).*

(Continued)

*Primary Examiner* — Sath V Perungavoor
*Assistant Examiner* — Kate Luo
(74) *Attorney, Agent, or Firm* — Perkins Coie LLP

(57) ABSTRACT

The present Invention relates to a camera system suitable for use in minimally invasive surgery (MIS), among other applications. In at least one embodiment, the camera system includes an autonomous miniature camera, a light source assembly providing features such as steerable illumination and a variable radiation angle, and a control and processing unit for processing images acquired by the camera Io generate improved images having reduced blurring using a deblurring algorithm.

20 Claims, 7 Drawing Sheets

(56) References Cited

U.S. PATENT DOCUMENTS

| | | |
|---|---|---|
| 5,446,591 A | 8/1995 | Medlock |
| 5,526,446 A * | 6/1996 | Adelson et al. ............... 382/275 |
| 5,917,657 A | 6/1999 | Kaneko et al. |
| 6,081,388 A | 6/2000 | Widl |
| 6,188,526 B1 | 2/2001 | Sasaya et al. |
| 6,369,954 B1 | 4/2002 | Berge et al. |
| 6,618,208 B1 | 9/2003 | Silver |
| 6,737,646 B2 | 5/2004 | Schwartz |
| 6,891,682 B2 | 5/2005 | Aizenberg et al. |
| 6,956,975 B2 * | 10/2005 | Young ........................ 382/263 |
| 6,999,238 B2 | 2/2006 | Glebov et al. |
| 7,126,903 B2 | 10/2006 | Feenstra et al. |
| 7,256,943 B1 | 8/2007 | Kobrin et al. |
| 7,367,550 B2 | 5/2008 | Lee |
| 2001/0017985 A1 | 8/2001 | Tsuboi et al. |
| 2002/0176148 A1 | 11/2002 | Onuki et al. |
| 2003/0095336 A1 | 5/2003 | Floyd |
| 2003/0117511 A1 * | 6/2003 | Belz et al. ................ 348/333.11 |
| 2005/0068586 A1 * | 3/2005 | Sano .............................. 358/2.1 |
| 2006/0187308 A1 * | 8/2006 | Lim et al. ................... 348/208.4 |

OTHER PUBLICATIONS

Tian et al. ("An Ant Colony Optimization Algorithm for Image Edge Detection" IEEE Congress on Computational Intelligence Jun. 2008).*

Bahadir, K. et al., "Color Plane Interpolation Using Alternating Projections," IEEE Transactions on Image Processing, 11(9):997-1013, Sep. 2002.

Banham, M.R., et al., "Digital Image Restoration," IEEE Signal Processing Magazine, 14(2):24-41, Mar. 1997.

Tzeng, J., et al., "Image Enhancement for Fluid Lens Camera Based on Color Correlation," IEEE Transactions on Image Processing, 18(4):729-739, Apr. 2009.

Tzeng, J., et al., "Multi-Band Color Image Deblurring Using Contourlets for Fluid Lens Camera Systems," 2009 16th IEEE International Conference on Image Processing (ICIP), pp. 713-716, Nov. 2009.

* cited by examiner

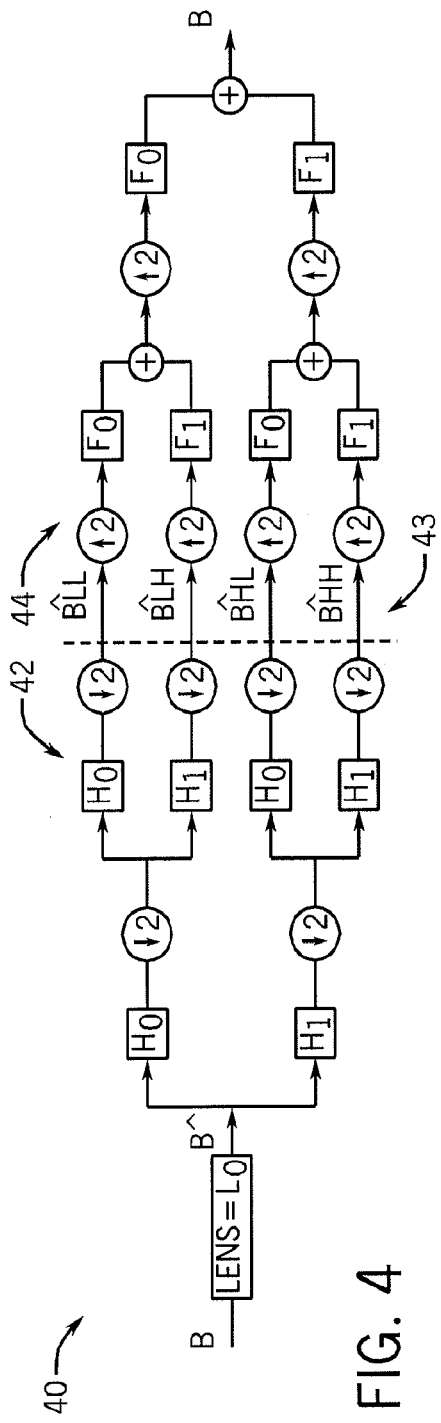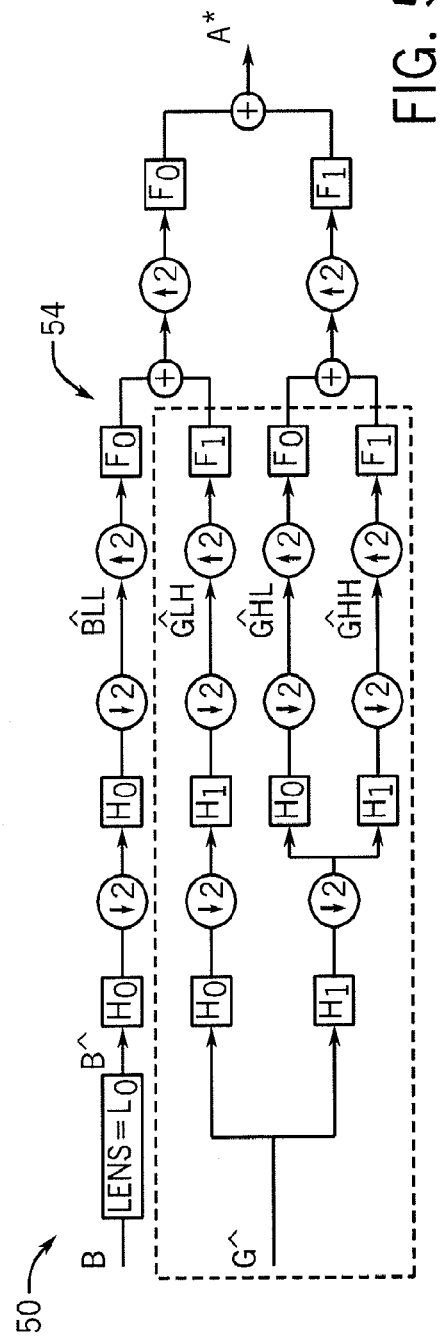

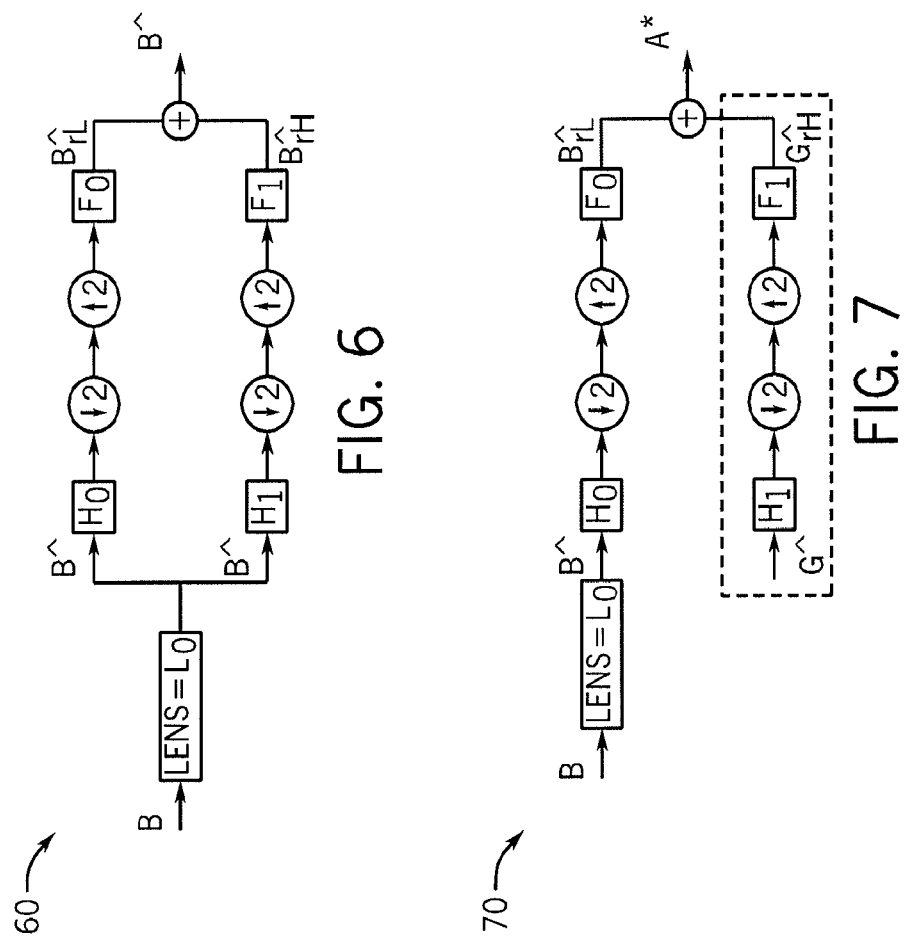

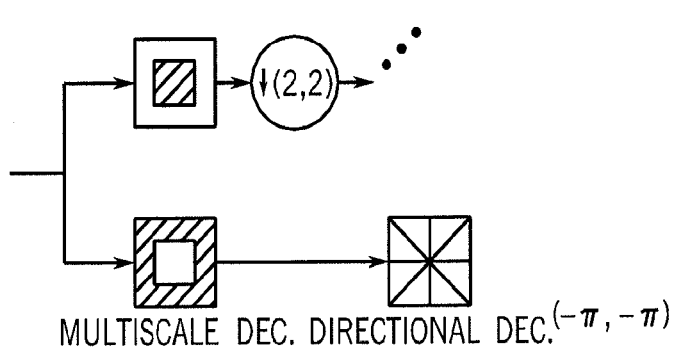
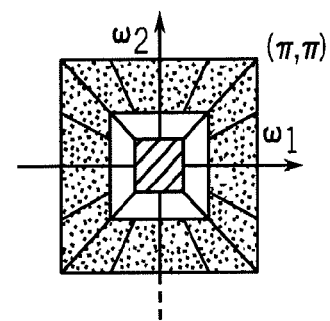
FIG. 8a  FIG. 8b
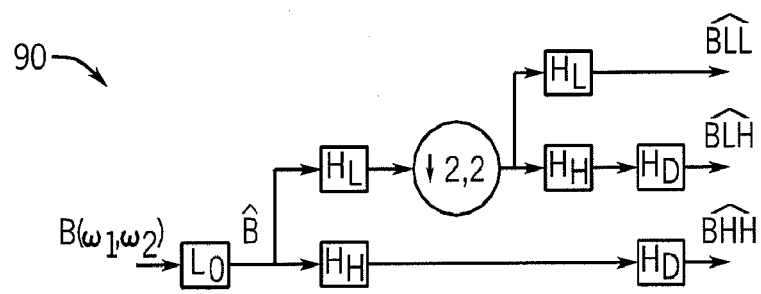
FIG. 9

FIG. 10a
$$\widehat{BLH} = 0.25 H_D(\omega_1,\omega_2) H_H(\omega_1,\omega_2) [\sum_{m=0}^{1}\sum_{n=0}^{1} H_L(\frac{\omega_1}{2}+n\pi, \frac{\omega_2}{2}+m\pi) L_0(\frac{\omega_1}{2}+n\pi, \frac{\omega_2}{2}+m\pi) B(\frac{\omega_1}{2}+n\pi, \frac{\omega_2}{2}+m\pi)]$$

FIG. 10b
$$|BLH - \widehat{GLH}|^2 < |BLH - \widehat{BLH}|^2$$

FIG. 10c
$$\alpha = 0.25 H_D(\omega_1,\omega_2) H_H(\omega_1,\omega_2) H_L(\frac{\omega_1}{2},\frac{\omega_2}{2})$$
$$\alpha^2 [B(\frac{\omega_1}{2},\frac{\omega_2}{2}) - \hat{G}(\frac{\omega_1}{2},\frac{\omega_2}{2})]^2 < \alpha^2 [B(\frac{\omega_1}{2},\frac{\omega_2}{2}) - L_0(\frac{\omega_1}{2},\frac{\omega_2}{2}) B(\frac{\omega_1}{2},\frac{\omega_2}{2})]^2$$

FIG. 10d
$$[1 - \frac{\hat{G}(\frac{\omega_1}{2},\frac{\omega_2}{2})}{B(\frac{\omega_1}{2},\frac{\omega_2}{2})}]^2 < [1 - L_0(\frac{\omega_1}{2},\frac{\omega_2}{2})]^2$$

FIG. 10e
$$0 < [\frac{\hat{G}(\frac{\omega_1}{2},\frac{\omega_2}{2})}{B(\frac{\omega_1}{2},\frac{\omega_2}{2})} - L_0(\frac{\omega_1}{2},\frac{\omega_2}{2})][2 - L_0(\frac{\omega_1}{2},\frac{\omega_2}{2}) - \frac{\hat{G}(\frac{\omega_1}{2},\frac{\omega_2}{2})}{B(\frac{\omega_1}{2},\frac{\omega_2}{2})}]$$

FIG. 10f
$$L_0(\frac{\omega_1}{2},\frac{\omega_2}{2}) < \min[\frac{\hat{G}(\frac{\omega_1}{2},\frac{\omega_2}{2})}{B(\frac{\omega_1}{2},\frac{\omega_2}{2})}, 2 - \frac{\hat{G}(\frac{\omega_1}{2},\frac{\omega_2}{2})}{B(\frac{\omega_1}{2},\frac{\omega_2}{2})}]$$
$$L_0(\frac{\omega_1}{2},\frac{\omega_2}{2}) > \max[\frac{\hat{G}(\frac{\omega_1}{2},\frac{\omega_2}{2})}{B(\frac{\omega_1}{2},\frac{\omega_2}{2})}, 2 - \frac{\hat{G}(\frac{\omega_1}{2},\frac{\omega_2}{2})}{B(\frac{\omega_1}{2},\frac{\omega_2}{2})}]$$

FIG. 10g
$$\hat{B}(\frac{\omega_1}{2},\frac{\omega_2}{2}) < \min[\hat{G}(\frac{\omega_1}{2},\frac{\omega_2}{2}), 2B(\frac{\omega_1}{2},\frac{\omega_2}{2}) - \hat{G}(\frac{\omega_1}{2},\frac{\omega_2}{2})]$$
$$\hat{B}(\frac{\omega_1}{2},\frac{\omega_2}{2}) > \max[\hat{G}(\frac{\omega_1}{2},\frac{\omega_2}{2}), 2B(\frac{\omega_1}{2},\frac{\omega_2}{2}) - \hat{G}(\frac{\omega_1}{2},\frac{\omega_2}{2})]$$

CAMERA SYSTEM WITH AUTONOMOUS MINIATURE CAMERA AND LIGHT SOURCE ASSEMBLY AND METHOD FOR IMAGE ENHANCEMENT

CROSS-REFERENCE TO RELATED APPLICATIONS

This application claims the benefit of U.S. provisional patent application no, 61/105,542 entitled "Camera System With Autonomous Miniature Camera And Light Source Assembly And Method For Image Enhancement Using Color Correlation" filed on Oct. 15, 2008, which is hereby incorporated by reference herein.

STATEMENT REGARDING FEDERALLY SPONSORED RESEARCH OR DEVELOPMENT

FIELD OF THE INVENTION

The present invention relates to camera systems and methods and, more particularly, to systems and methods of lighting that are employed as part of (or in combination with) such camera systems and methods in any of a variety of applications and environments including, for example, medical applications and environments,

BACKGROUND OF THE INVENTION

Minimally invasive surgery (MIS) is a modern surgical technique in which operations in the abdomen and thorax or elsewhere are performed through small incisions in the skin. Since 1981, when the first laparoscopic cholecystectomy (gallbladder removal) was performed, this surgical field has greatly improved due to various technological advances. Today this operation typically uses 3-6 abdominal skin incisions (each approximately 5-12 mm in length), through which optical fibers, cameras, and long operating instruments are inserted into the abdominal cavity. The abdomen is usually insufflated (inflated) with carbon dioxide gas to create a working and viewing space and the operation is performed using these long instruments through the incisions, images acquired by way of one or more camera devices inserted into the working and viewing space are viewed on a TV monitor beside the patient as the surgery progresses.

One currently available camera for MIS is composed of a 12-15-inch long tube containing several lenses and optical fibers (the laparoscope). The front section of the laparoscope enters the abdomen through a portal called a "trocar" and the back end is connected to a power source, light source and supporting hardware through large cables protruding from the rear of the scope. The internal optical fibers convey xenon or halogen light via an external light source into the internal cavity and the lenses transfer the images from within the cavity to an externally connected portable video camera. Disadvantages of this imaging device include its two-dimensional view, lack of sufficient optical zoom, inability to adjust its angle of view or angle of illumination without a new incision, inability to control light intensity, and restrictions on its movement due to its large size and external cables. This is especially significant in this era of MIS in which it is desired to minimize the number and extent of incisions, and wherein new technologies are being developed such as Natural Orifice Translumenal Endoscopic Surgery (NOTES) which use no abdominal incisions at all, but instead utilize a single trocar inserted into the mouth or vagina to carry all surgical instruments as well as the camera and light source.

Lighting has been a challenge for laparoscopic cameras because they operate in an environment of extreme darkness where accessibility to sources of illumination is limited. Further, new cameras are being utilized which possess features such as a flexible field of view or optical zoom capability. Although such camera features are extremely desirable insofar as they allow surgeons to obtain both the global and the detailed view of the patient's abdomen as well as a large working space to practice surgery, it results in more strict requirements on lighting.

More particularly, current light sources including halogen and LED lamps are designed to have a fixed radiation pattern characterized by a full-width half intensity angle. For those cameras for which zoom is an option, when a surgeon wants to see the details of an organ in a zoom-in mode, the angle of illumination may be much greater than the camera's field-of-view and thus there is often insufficient lighting for the desired image resulting in poor quality of the acquired image. On the other hand, when a surgeon operates the camera in zoom-out mode to achieve a wide field-of-view, the limited illumination angle of the light source may not cover the entire desired image area, leading to rapid fading of the acquired image towards the edge of the image field. In addition, the center portion of the acquired image may be over illuminated and saturated, resulting in penalty in resolution and dynamic range.

For at least the above-described reasons, therefore, it would be advantageous if an improved system and method for illumination capable of being employed along with cameras as are used in a variety of applications including, for example MIS applications, could be developed.

Further, images corresponding to one or more color channels of the camera can be blurred, and it would be advantageous if an improved deblurring method could be developed to provide enhanced image quality.

SUMMARY OF THE INVENTION

The present inventors have recognized that such an improved system and method for illumination can be provided through the use of one or more tunable lenses as part of the light source. Tunable lenses refer to lenses with variable focal distances, and one type of a tunable lens is a fluidic lens. By utilizing such tunable lenses, which in at least some embodiments are fluidic (or microfluidic) lenses, improved lighting particularly involving a timed radiation pattern and/or a controlled beam angle can be achieved.

In at least one embodiment, the present invention relates to a camera system suitable for use in minimally invasive surgery (MIS). The camera system includes an autonomous miniature camera, a light source assembly providing features such as steerable illumination, a variable radiation angle and auto-controlled light intensity, and a control and processing unit for processing images acquired by the camera to generate improved images having reduced blurring using a deblurring algorithm which correlates information between colors.

In at least one additional embodiment, the present invention relates to a camera system for MIS having one or more autonomous miniature cameras enabling simultaneous multi-angle viewing and a three dimensional (3D) view, and a light source assembly having a light source with a tunable radiation pattern and dynamic beam steering. The camera is insertable into an abdominal cavity through the standard portal of the procedure, either through a trocar or via natural orifice. The light source assembly is also insertable through the same portal. The camera system also preferably includes a control and processing unit for independently controlling the camera (pan, tilt and zoom) and the light source assembly. Wireless network links enable communication between these system components and the control and processing unit, eliminating bulky cables. The control and processing unit receives location signals, transmits control signals, and receives acquired image data. The control and processing unit processes the acquired image data to provide high quality images to the surgeon.

In such an embodiment, the tunable and steerable nature of the light source assembly allows light to be efficiently focused primarily on the camera field of view, thereby optimizing the energy directed to the region of interest. The autonomous nature of the camera and light source assembly (in terms of location and movement) allows the camera to be freely movable within the abdominal cavity to allow multiple angles of view of a region of interest (such as target organs), with the light source assembly capable of being adjusted accordingly. In this manner, although camera motion tracking is required, the illumination can be adjusted to reduce glare and provide optimal lighting efficiency.

In still another embodiment of the present invention, the camera includes a fluidic lens system which causes at least one color plane (channel) of acquired images to appear sharp and the other color planes (channels) to appear blurred. Therefore, another aspect of the invention provides a deblurring algorithm for correcting these blurred color planes of acquired images from the camera. The algorithm uses an adapted perfect reconstruction filter bank that uses high frequency sub-bands of sham color planes to improve blurred color planes. Refinements can be made by adding cascades and a filter to the system based on the channel characteristics. Blurred color planes have good shading information but poor edge information. The filter band structure allows the separation of the edge and shading information. During reconstruction, the edge information from the blurred color plane is replaced by the edge information from the sharp color plane.

Further, in at least one embodiment, the present invention relates to a camera system configured to acquire image information representative of subject matter within a selected field of view. The camera system includes a camera that receives reflected light and based thereon generates the image information, and a light source assembly operated in conjunction with the camera so as to provide illumination, the light source assembly including a first light source and a first tunable lens. At least some of the illumination output by the light source assembly is received back at the camera as the reflected light. Additionally, the tunable lens is adjustable to vary the illumination output by the light source assembly, whereby the illumination can be varied to substantially match the selected field of view.

Further, in at least one additional embodiment, the present invention relates to a method of operating a camera system to acquire image information representative of subject matter within a selected field of view. The method includes providing a camera and a light source assembly, where the light source assembly includes a light source and a tunable lens. The method also includes controlling the tunable lens, and transmitting the light beam from the light source assembly. The method additionally includes receiving reflected light at the camera, where at least some of the light of the light beam transmitted from the light source assembly is included as part of the reflected light, and where the image information is based at least in part upon the reflected light. The tunable lens is controlled to vary the light beam output by the light source assembly, whereby the light beam can be varied to substantially match the selected field of view.

Further, in another aspect of the present invention, a fluidic lens camera system including an image sensor is used for acquiring image data of a scene within a field of view of the camera. Image data is provided from each of a plurality of color channels of the image sensor, such as red (R), green (G), and blue (B) color channels. A control and processing unit is operable to receive and process the acquired image data in accordance with image processing methods described below to correct the blurred image data. Briefly, wavelet or contourlet transforms can be used to decompose the image data corresponding to the different color channels, mesh the edge information from a sharp color channel with the non-edge information from a blurred color channel to form a set of sub-band output coefficients or reconstruction coefficients in the wavelet or contourlet domain, and then reconstruct a deblurred image using these sub-band output coefficients.

In one embodiment, the decomposition and reconstruction steps use a modified perfect reconstruction filter bank and wavelet transforms. In another embodiment, the decomposition and reconstruction steps use a contourlet filter bank, contourlet transforms, and an ant colony optimization method for extracting relevant edge information.

In another embodiment, a method for deblurring a blurred first color image corresponding to a first color channel of a camera that also produces a sharp second color image corresponding to a second color channel of the camera is provided, wherein the first and the second color images each include a plurality of pixels with each pixel having an associated respective value. The method includes decomposing the first color image by filtering and upsampling to generate a first set of one or more first sub-band output coefficients, wherein each first sub-band output coefficient corresponds to a respective sub-band in a selected one of a wavelet and a contourlet domain, and decomposing the second color image by filtering and upsampling to generate a second set of second sub-band output coefficients, wherein each second sub-hand output coefficient corresponds to a respective sub-band in the selected domain. The method further includes selecting those second sub-band output coefficients that represent edge information, each of the selected second ruby band output coefficients corresponding to a respective selected sub-band, with the selected sub-bands together defining an edge sub-band set, and preparing a third set of sub-band output coefficients which includes the selected second sub-band output coefficients representing edge information and at least one first sub-band output coefficient corresponding to a sub-band other than those sub-bands in the edge sub-band set. A deblurred first color image is reconstructed by upsampling and filtering using the third set of sub-band output coefficients as input.

Additionally, in at least some further embodiments, the present invention relates to a light source assembly. The light source assembly includes an output port, a light source, and a tunable lens positioned between the first light source and the output port. The light source generates light that passes through the tunable lens and then exits the light source assembly via the output port as output light, and the tunable lens is adjustable to vary a characteristic of the output light exiting the light source assembly via the output port. In at least some of the above embodiments, the light source includes an array of light emitting diodes (LEDs) that each can be controlled to be turned on or turned off and, based upon such control, a direction of light exiting the light source assembly can be varied.

BRIEF DESCRIPTION OF THE DRAWINGS

FIG. 4 illustrates a perfect reconstruction filter bank for decomposing and reconstructing an image;

FIG. 5 illustrates a modified perfect reconstruction filter bank;

FIG. 6 illustrates a one dimensional perfect reconstruction filter bank;

FIG. 7 illustrates a modified one dimensional perfect reconstruction filter bank;

FIGS. 8a-8b illustrate a contourlet transform and the resulting frequency division in a contourlet frequency domain;

FIG. 9 illustrates an exemplary two dimensional contourlet filter bank; and

FIGS. 10a-10g illustrate a various conditions for a contourlet filter bank.

DETAILED DESCRIPTION OF THE PREFERRED EMBODIMENT

Figure 1:
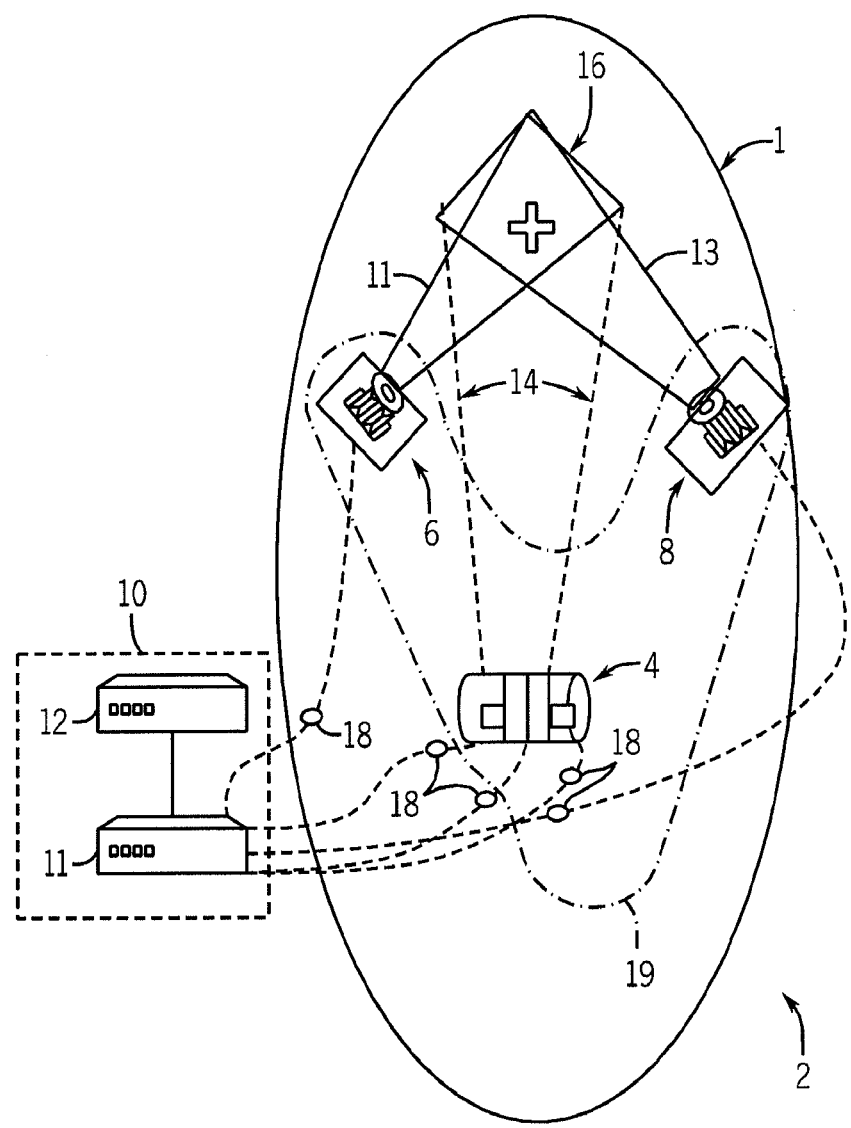
FIG. 1 is a schematic view of an exemplary camera system in accordance with at least one embodiment of the present invention.

Referring to FIG. 1, an exemplary embodiment of a camera system 2 includes a miniature camera 4, two light source assemblies 6 and 8, respectively, and a control and processing unit 10 which includes a control unit 11 and a PZT (piezoelectric transducer) operator control unit 12 that are coupled to and in communication with one another. As shown schematically, the miniature camera 4 and light source assemblies 6, 8 are placed within an abdominal cavity 1 (or other body cavity or the like) of a patient, while the control and processing unit 10 remains exterior to the body of the patient. In at least one embodiment, the camera is insertable into an abdominal cavity through a 20 mm incision, such as on the abdominal wall, and the light source assembly is also insertable through an incision. In the present embodiment, it is envisioned that the miniature camera 4 is physically separated from each of the light source assemblies 6, 8, each of which is also physically separate from one another. Nevertheless, as represented by a dashed line 19, in other embodiments, it is possible for the miniature camera 4 and the light source assemblies 6, 8 (or, alternatively, one of those light source assemblies), to be physically connected or attached, or even to be housed within the same housing.

The camera system 2 is adjusted such that a field of view 14 of the camera 4 encompasses a desired region of interest (which in this example is a quadrilateral) 16 within the abdominal cavity 1, and thus encompasses subject matter within that desired region of interest (e.g., a particular organ or portion of an organ). As discussed further below, the light source assemblies 6, 8 are respectively adjusted to generate light beams 11, 13, respectively, which provide efficient illumination to the field of view 14 so as to effectively illuminate the desired region of interest 16 and subject matter contained therein. Some or all of the light directed to the desired region of interest 16 and generally to the field of view 14 is reflected off of the subject matter located there and consequently received by the miniature camera 4 as image information. In at least some embodiments, an effort is made to control the light provided by the light source assemblies 6, 8 so that the region illuminated by the light exactly corresponds to (or tills upon), or substantially corresponds to, the field of view 14. Given the adjustability of the light source assemblies in such manner, in at least some embodiments the light source assemblies (or light sources) can be referred to as "smart light source assemblies" or ("smart light sources").

As will be described in more detail below with respect to FIGS. 2A-2C and 3A-3C, in the present embodiment, the miniature camera 4 includes a light sensor and a fluidic lens (e.g., microfluidic lens) system. The light sensor can take a variety of forms, for example, that of a complementary metal-oxide-semiconductor (CMOS) or that of a charge coupled device (CCD) sensor. In the present embodiment, the fluidic lens system of the miniature camera 2 affects different color wavelengths non-uniformly. Although in the present embodiment a fluidic lens system is employed, in other embodiments other types of lens systems including other tunable lens systems can be employed instead (or in addition to) a fluidic lens system. Typically the lens system employed will afford the camera with at least some zooming capability. Further, the control unit 11 and piezoelectric (PZT) operator control unit 12 can take a variety of forms depending upon the embodiment. In one embodiment, each of the control units 11, 12 includes a processing device (e.g., a microprocessor) and a memory device, among other components. Also, while the control and processing unit 10 is shown to include both the control unit 11 and the PZT operator control unit 12, in other embodiments the functioning of those two control units can be performed by a single device.

During operation, the miniature camera 4 of the camera system 2 acquires images (e.g., acquired image data) of the desired region of interest 16 within the field of view 14, which are transmitted to the control and processing unit 10. In one embodiment, the miniature camera 4 transmits, over 3 Channels, two video images and additionally the optical zoom state. The control unit 11 (e.g., a master computer) of the control and processing unit 10 processes the received data, and can further transmit to the light source assemblies 6, 8 any changes that should be made in their operation so as to adjust the intensity and/or direction/angle of the light emitted from the light source assemblies. Among other things, the control and processing unit 10 (particularly the control unit 11) provides color corrections to the acquired images using a deblurring algorithm, as more fully described below.

Although shown with the single miniature camera 4 and the two light source assemblies 6, 8, the system can in other embodiments include any arbitrary number of light source assemblies and any arbitrary number of cameras. Although only a single light source assembly can be used in some embodiments, the use of the multiple light sources 6, 8 so as to provide illumination from different angles in the present embodiment does afford greater efficiencies. Further, the use of multiple light sources from different angles can make possible additional types of image processing. For example, different lighting angles and shadows can be processed to create enhanced three-dimensional images and anatomical landmarks identification.

Still referring to FIG. 1, in the present embodiment a two-way wireless communication network having wireless communication links 18 is provided that allows for the transmission of control and/or monitoring signals between/among components of the system 2. The wireless communication links 18 among other things allow for communication between the control unit 11 and the miniature camera 4. More particularly in this regard, the wireless communication links 18 allow for signals to be transmitted from the miniature camera 4 back to the control unit 11, particularly signals representative of video images from inside the abdominal cavity as detected by the miniature camera. Also, the wireless communication links 18 allow for control signals to be provided from the control and processing unit 10 to the miniature camera 4 for the purpose of governing the pan, tilt, and zoom of the camera lens. Optical zoom information and any camera motion information can be further taken into account by the control unit 11 in its processing of image data.

Additionally, the wireless communication links 18 allow for communication between the control unit 11 and the light source assemblies 6, 8 so as to allow for control over the on/off status, brightness, beam orientation and/or other operational characteristics of the light source assemblies. In at least some embodiments, the control and processing unit 10 receives video imaging and zoom data, processes it, and according to the change of optical zoom and motion estimation, transmits appropriate control signals to the lens and the light source assemblies.

Although not shown, it will be understood that the control and processing unit 10 as well as the components internal to the abdominal cavity 1 (or other body cavity or other space), such as the miniature camera 4 and the light source assemblies 6, 8, can each include a wireless transceiver or other conventional wireless communications hardware allowing for the establishment of the wireless communication links 18. The use of the wireless communication links 18 for the purpose of allowing for communication of control and monitoring signals between the control and processing unit 10 (and particularly the control unit 11) and each of the miniature camera 4 and light source assemblies 6, 8 eliminates the need for cables extending through the wail of the abdomen 1 for such purpose.

In at least some embodiments, the control and processing unit 10 coordinates all wireless communications between the components of the camera system 2. Further, in at least some embodiments, some or all wireless communications are achieved by way of conventional signal processing algorithms and networking protocols. For example, in one embodiment, the miniature camera 4 transmits to the control and processing unit 10 in three channels the two video images (for example, the G and B channels) and the optical zoom state. Further for example, in one embodiment, the wireless communication links 18 employ Wi-Fi car Bluetooth communication protocols/technologies. Additionally, depending on video resolution, frame rate, the distance between the control and processing unit 10 and the miniature camera 4 (or cameras), as well as the number of cameras in circumstances where more than one such camera is used, it can become desirable to compress the video bit streams. Possible compression algorithms include, for example, the simple image coding PEG standard, the high-end image coding JPEG2000 standard, and the high-end video coding H.264 standard, as well as Scalable Video Coding. The algorithm choice depends on other factors such as algorithm complexity, overall delay, and compression artifacts.

Additionally, it will be understood that the portions of the camera system 2 within the abdominal cavity 1 (again, the miniature camera 4 and the light source assemblies 6, 8) are autonomous and freely movable within the abdominal cavity, which among other things allows for the desired region of interest 16 to be viewed from multiple directions/angles. Allowing for multiple angles of views can be desirable in a variety of circumstances, for example, when the desired region of interest 16 includes multiple target organs, or target organs with complicated surface shapes. In at least one embodiment, an operator (e.g., a physician) using the PZT operator control unit 12 is able to provide instructions to the control and processing unit 10 (the PZT operator control unit can include input devices allowing for the operator to provide such instructions), based upon which the control and processing unit 10 in turn causes changes in the position(s) of one or both of the light source assemblies 6, 8 in relation to (and, in some cases, so as to become closer to) the desired region of interest 16. Such modifications in the position(s) of the light source assemblies 6, 8 can in some circumstances save energy and provide a longer illumination period notwithstanding battery powering of the light source assemblies.

In at least some embodiments, the particular positions of the light source assemblies 6, 8 and the miniature camera 4 are set up at a particular time during an operation (e.g., by insertion into the abdominal cavity 1 by a physician early on during an operation) and then those positions are fixed during the remainder of the operation. In such cases, the relative locations of the light source assemblies 6, 8 and the miniature camera 4 can be computed at an initial set up stage. The initial parameters for the light beams 11, 13 provided by the light source assemblies 6, 8 (e.g., angles and beam direction) as well as for the miniature camera 4 (e.g., viewing angles with respect to the light beams) are also computed. In some embodiments, additional movements of the light source assemblies 6, 8 and/or the miniature camera 4 can also be tracked. In some such embodiments, to calculate the light angle modification (or a desired light angle modification), ongoing information regarding the spatial locations of the miniature camera 4, light source assemblies 6, 8, and in at least some cases also the control and processing unit 10 is obtained by triangulation of the wireless signals captured from each component using any of various conventional triangulation techniques. Additionally as discussed in further detail below, in at least some embodiments, the illumination emitted from the light source assemblies 6, 8 can further be adjusted as necessary.

Given the particular features of the miniature camera 4 as described above and further below, the miniature camera provides several advantageous features. In particular, in the present embodiment the miniature camera 4 is small in size, has powerful optical zoom capabilities, and has few or no moving parts while zooming. The powerful optical zooming afforded by the miniature camera 4 allows the miniature camera to be distant from the desired region of interest 16. Consequently, while if the light source assemblies 6, 8 were physically connected to the miniature camera 4, a significant amount of illumination would potentially be wasted (in that it would not reach the desired region of interest 16), in the present this need not occur. Rather, instead of placing the light source assemblies 6, 8 on (or otherwise physically connecting those assemblies to) the miniature camera 4, in the present embodiment the light source assemblies are separate from and can be moved independently of the miniature camera 2.

Figure 2A:
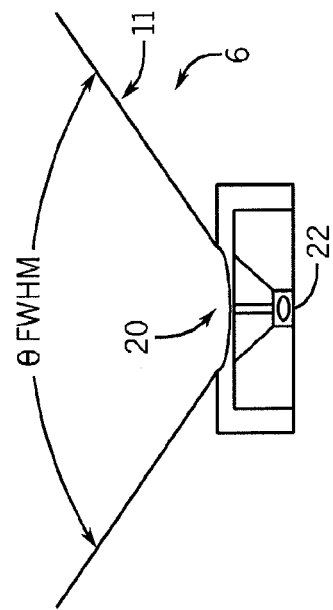
FIGS. 2A-2C respectively show three different schematic views of an exemplary light source assembly using an LED and a microfluidic lens, illustrating various tunable radiation patterns achievable by adjusting the lens.
Figure 2B:
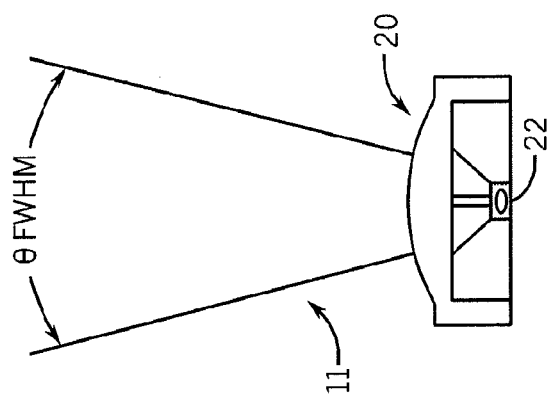
Figure 2C:
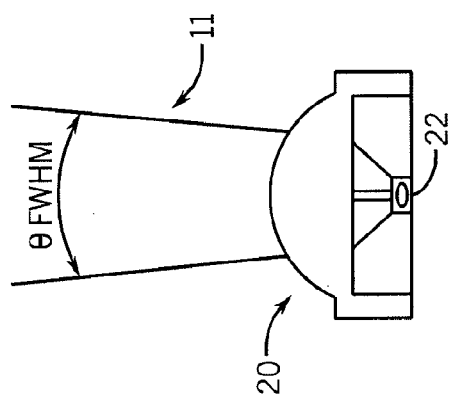

Turning now to FIGS. 2A-2C, one of the light source assemblies 6, 8, namely, the light source assembly 6, is shown schematically in more detail (in cross-section) in three different operational circumstances. It will be understood that, in the present embodiment, each of the light source assemblies 6, 8 is identical in construction and operation, albeit in other embodiments the various light sources need not be identical. As shown in each of FIGS. 2A-2C, the light source assembly 6 includes a tunable lens that in the present embodiment is a microfluidic lens 20 (albeit in other embodiments other types of tunable lenses can be employed as well), and additionally a light emitting diode (LED) 22. The LED 22 is small (typically about 1 $mm^2$ including package) and can be a widely available, off the shelf component that is of low cost, and that can easily be mounted on a printed circuit board (also not shown) so as to form a surface-mount LED or the like.

Although not shown, the light source assembly 6 further should be understood as including a power source such as a battery. Having an integrated power source to supply power to the light source assembly 6 is advantageous because, by using such a structure, there is no need to employ cables going through the abdominal wall into the abdominal cavity 1 (albeit this limits the amount of power available and further increases the need for focusing the light to the desired region of interest 16 rather than illuminating a large unrecorded field beyond the desired region of interest).

In the present embodiment, the microfluidic lens 20 (and, indeed, any microfluidic lens or lenses employed in the camera 4 as well) can be a microfluidic lens such as that described in U.S. patent application Ser. No. 11/683,141, which was filed on Mar. 7, 2007 and is entitled "Fluidic Adaptive Lens Systems and Methods" (and which issued as U.S. Pat. No. 7,453,646 on Nov. 18, 2008), which is hereby incorporated by reference herein. The microfluidic lens 20 is placed a few millimeters away from the LED 22 (although this separation distance is not shown FIGS. 2A-2C) and has a tunable focal length and appropriate aperture typically several times the dimension of the LED die. For example, if the LED die is 1 mm×1 mm (i.e., 1 mm$^2$), the clear aperture of the tunable lens can be 3 mm by 3 mm (i.e., 9 mm$^2$) or greater. By adjusting the focal length of the microfluidic lens 20, the radiation pattern (e.g., radiation angle) of each light source can be dynamically adjusted to obtain optimal illumination to match varying fields of view of the camera. That is, the light beam 11 emanating from the light source assembly 6 can be varied in this manner.

To illustrate this effect, FIGS. 2A, 2B and 2C in particular respectively show medium, narrow and wide radiation patterns (particularly the extent of an angle $\theta_{FWHM}$ corresponding to full width at half maximum intensity) corresponding to three versions of the light beam 11 that are generated by the same light source assembly 6 when the microfluidic lens 20 is tuned to three different settings. More particularly as shown, the narrow and medium radiation patterns are achieved when the microfluidic lens 20 is tuned so as to be highly-convex and moderately convex, respectively, while the wide radiation pattern is achieved when the microfluidic lens is tuned so as to be concave. In the present embodiment, the distance between the LED 22, and the microfluidic lens 20 in the light source assembly 6 is close enough (e.g. 3-5 mm) so that, even for the shortest focal distance of the lens, the light of the LED is "defocused" rather than being "focused". The defocused LED light radiates at a divergent angle.

Notwithstanding the exemplary radiation patterns shown in FIGS. 2A-2C, assuming that the microfluidic lens 20 has an ultrawide tuning range, the radiation angle of illumination can be controlled to vary within a wide range of approximately 15 degrees to 140 degrees. The optimal illumination condition is achieved when the radiation pattern produced by the light source assembly 6 is about 20% greater than the field-of-view 14 of the miniature camera 4. For a 4× optical zoom camera with a field-of-view of 25 to 100 degrees, the corresponding desired illumination angles range from 30 to 120 degrees, well within the capability of the above-described light source assembly 6. As a result, for any chosen field of view of a miniaturized camera, the subject matter within the field of view will be uniformly illuminated for the best image quality.

Figure 3C:
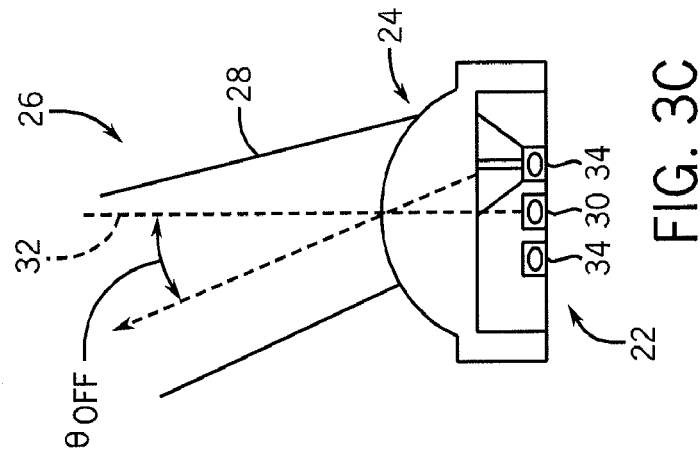
FIGS. 3A-3C respectively show three different schematic views of another embodiment of a light source assembly using LED arrays and a microfluidic lens, illustrating dynamic beam steering by selection and energization of one or more LEDs in the array.
Figure 3B:
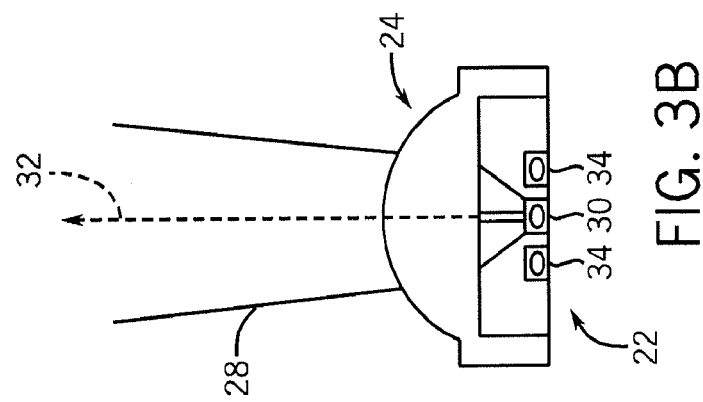
Figure 3A:
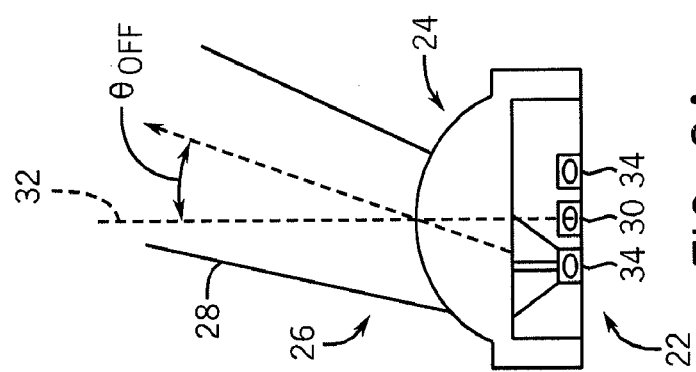

Turning to FIGS. 3A-3C, another embodiment of a light source assembly 26 is shown in simplified schematic form a in three different views (again in cross-section). The light source assembly 26 can be used in place of either of the light source assemblies 6, 8 discussed above. The light source assembly 26 in particular allows for steering of an illumination beam 28 emanating from the light source assembly, so as to allow for efficient illumination of various different desired regions of interest (e.g., the region of interest 16) without requiring mechanical movement of the light source so that it can shine upon those different regions. In some circumstances, such steering of the illumination beam 28 also allows for efficient illumination of a given desired region of interest from different directions/angles.

While in this embodiment the light source assembly 26 (like the light source assembly 6 of FIGS. 2A-2C) again includes both a tunable fluidic (again in this embodiment, microfluidic) lens 24 and a LED light source, in this embodiment the LED light source includes not merely one LED but rather includes an array of multiple LEDs 22 adjacent the lens 24. Depending upon the embodiment, the array 22 can take a variety of forms, employ any arbitrary number of LEDs, and/or employ LEDs of any arbitrary color(s). In the present exemplary embodiment, the array 22 particular has a center LED 30 aligned with a central axis 32 of the lens 24, and six additional LEDs 34 arranged along a concentric ring extending around the center LED 30 in manner where each of the additional LEDs is spaced apart by the same distance from each of its three neighboring LEDs (that is from the center LED and from each of the neighboring LEDs along the concentric ring). Thus, in the cross-sectional views provided by FIGS. 3A-3C, the center LED 30 and two of the six additional LEDs are visible (it will be understood that the remaining four additional LEDs would be fore or aft of the three visible LEDs, that is, into or out of the page when viewing FIGS. 3A-3C).

As further shown in FIGS. 3A-3C, by selectively turning on or off the different ones of the LEDs so that the different LEDs are illuminated, the same light source assembly 26 given the same tuning of the lens 24 is capable of producing light beams 28 that have different orientations. More particularly, as shown in FIG. 3B, when the center LED 30 is turned on and the additional LEDs 34 are all shut off, the light beam 28 is aligned (that is, centered about) the central axis 32 of the lens 24. By comparison, as shown in FIGS. 2A and 2C, given proper design of the lens aperture and the f-number of the lens 24, when the respective additional LEDs 34 on the concentric ring are energized (and the center LED 30 is shut off), the light beams 28 produced are light cones that are angularly offset from the central axis 32 (by amounts $\theta_{OFF}$). More particularly, FIG. 2A illustrates a circumstance where the additional LED 34 to the left of the center LED 30 is energized, while FIG. 2C illustrates a circumstance where the additional LED to the right of the center LED is energized. The amount of angular offset in any given circumstance is determined by the particular spacing of the respective additional LEDs 34 (and also possibly, to some extent, by the tuning of the lens 24). As discussed with respect to FIGS. 2A-2C, the particular angles of divergence $\theta_{FWHM}$ of the light beams 28 are also determined by the tuning of the lens 24. That is, the light beams 28 are of a tunable divergent angle.

Given that different orientations of the light beams 28 can be achieved by energizing different ones of the LEDs 30, 34, it will be understood that beam steering can be achieved in the present embodiment without mechanical movement by selecting (and varying) which one(s) of the LEDs 30, 34 on or within the concentric ring are powered at any given time. While in the above example, only a single one of the LEDs 30, 34 is energized at a given time, in other embodiments multiple LEDs can also be powered simultaneously to create multiple beams along different directions, which can be desirable depending upon the particular desired regions of interest that are desirably illuminated, or to provide illumination suitable for supporting multiple cameras. As already noted, any of a variety of LED arrays having a variety of formations with any arbitrary number of LEDs can be utilized depending upon the embodiment. In other embodiments, additional LEDs and/or additional tunable lenses can be added to the assembly to achieve more finely-graded or quasi-continuous beam steering. That is, as the number of LEDs increases and/or the spacing between LEDs decreases, there is an increased ability to achieve finer steering of the light beams that are generated. Such quasi-continuous designs are more efficient and can allow for energy saving. Instead of illuminating a field that is composed of the margins between two LED areas by these two LEDs, the quasi-continuous design will illuminate the same area using only one LED.

Further, depending upon the embodiment, more than one lens can be utilized. For example, two or more lenses can be positioned sequentially between the LED(s) and the outer surface of the light source assembly through which emitted light leaves the light source assembly. Additionally, in the case of two or more lenses, the lenses can operate as a zoom lens system but in a reverse sense. Like a zoom lens capable of continuously varying its magnification factor, a dual tunable-lens system can continuously vary the orientation of the radiation pattern without physically tilting the device. Through the use of multiple lenses in addition to multiple LEDs (particularly as LED array with a large number of LEDs), truly, continuous beam steering can be achieved. Again, such truly continuous beam steering can be more energy-efficient in providing desired illumination.

To summarize, as illustrated by FIGS. 2A-3C, in at least some embodiments of the present invention the emitted light can be controlled in two respects, namely, the area and the location of illumination. In at least some embodiments, in order to control the area of illumination, a fluidic tunable lens positioned in front of the light source is controlled. Depending on the optical zoom used by the camera, the emitted light will be adjusted to a narrow or wide radiation pattern by changing the shape of the lens. Further, in at least some embodiments, in order to control the location of the center of the beam of emitted light relative to a center axis of the lens, control signals can be generated to select and power desired LEDs in an LED array. By appropriately turning on and off different LEDs of the LID array, and/or appropriately tuning one or more microfluidic lenses, the beam emanating from the light source assembly can be steered. Further, by tracking the location of the camera and the light source assemblies (using the control and processing unit 10), both the radiation pattern and the direction of the light beam can be varied in a manner suited for illuminating arbitrary desired regions of interest.

As mentioned above, the camera 4 of the camera system 2 in at least some embodiments includes a tunable fluidic lens (for example, a microfluidic lens) system, and can be either a still camera or a video camera for acquiring a sequence of color images. The camera 4 includes an image sensor such as a CMOS sensor for acquiring images in each of a plurality of color channels, such as a red color channel (R), a green color channel (G), and a blue color channel (B). The images can be in the form of image data arrays, each corresponding to a respective one of the color channels and each comprising a plurality of pixels, with each pixel having an associated image value. As described below, some of the color channel images are blurred. Data from the image sensor can be transferred to the control and processing unit 10 to be further processed, and the corresponding images from each color channel can be combined to form a composite color image. The control and processing unit 10 can therefore perform a variety of image processing algorithms, including deblurring algorithms, which operate to enhance or correct any blurred images.

In particular, because the fluidic lens system of the camera affects different color wavelengths of light non-uniformly, different color wavelengths are focused at different focal depths resulting in the different R, B color channels having different amounts of blurring. The fluidic lens system can also cause non-uniform blurring in the spatial domain, making objects at the center of the field of view more blurred than objects near the outer borders. Thus, image enhancement and correction algorithms are desirable.

Thus, the control and processing unit can be programmed to perform various image processing algorithms, including an image processing technique for correcting for image warping and a technique for correcting blurred images. A warping correction technique can model the image warping taking into account both tangential and radial distortion components, a set of calibration parameters can be determined and the distortion can be inverted.

Various known deblurring techniques exist, such as Lucy-Richardson Deconvolution and Wiener filtering techniques, which have been used to correct for blur that occurs in glass lens systems. Both of these techniques require that an appropriate point spread function (PSF) be calculated, which can be a function of color, frequency, depth, and spatial location. Calculation of the PSF can be complex, cumbersome, and potentially inaccurate, making these techniques disadvantageous. Further, both techniques assume that the level of blur is the same for each of the color channels and do not account for the variations in blur between the color channels.

Generally, the deblurring methods described herein rely on the realization that edges in natural images occur at the same location in the different color channels. By adjusting the fluidic lens system and/or image sensor of the camera such that one color channel is sharp (at least relative to the others) even though the other color channels are blurred, it is possible to extract the edge information from the sharp image and use it in conjunction with non-edge information of the blurred image to produce a deblurred image. This is possible because the blurred color channels have good shading information but poor edge information.

In one embodiment, the fluidic lens system and/or CMOS sensor are adjusted such that the green channel is sharp and the red and blue channels are blurred, i.e., corresponding images are out of focus and have more blurring distortion. Then the acquired images from the camera can be processed (such as by the control and processing unit) to extract the edge information from the green image, and use it to correct the blurred images corresponding to each of the red and blue color channels. The images corresponding to each color channel can then be combined to produce a deblurred composite color image.

Basically, the image corresponding to the green color channel and the image corresponding to the red (or blue) color channel are both decomposed by filtering and downsampling using a filter bank that allows for the separation of the edge and the shading information. Edge information from the sharp green image is then meshed with the non-edge information for the red (or blue) image to form a set of sub-band output coefficients, and these are input to a reconstruction portion of the filter bank which includes upsampling, filtering and combining steps to generate a less blurred red (or blue) image and ultimately a less blurred composite color image. In one embodiment, decomposition is performed using wavelet decomposition and wavelet transforms, while in another embodiment contourlet decomposition and contourlet waveforms are used. In the case of the wavelet decomposition, the selection of which sub-band output coefficients to use in an image reconstruction can be determined a priori. In this regard, the sharp image is decomposed to obtain certain sub-band output coefficients which are each assumed to represent edge information (i.e., corresponding to sub-bands having a high frequency component) and the blurred image is decomposed to obtain other sub-band output coefficients corresponding to sub-bands which are assumed to not represent edge information (i.e., those sub-bands not having a high frequency component). In other words, the sub-bands for these sets do not overlap. The output coefficients from each are then combined to form an appropriate reconstruction set without any evaluation of whether the green output coefficients actually represent edge information.

In the case of contourlet decomposition, both the blurred and the sharp images can be decomposed to generate a corresponding sub-band output coefficient for each sub-band in a respective set of sub-bands, and the two sets of sub-bands can be overlapping sets. Then the resultant sub-band output coefficients corresponding to the sharp image can be evaluated to distinguish between strong and weak edges. For example, an ant colony optimization technique can be utilized to determine edge information, although other edge detection techniques can also be employed, in this case, a set of sub-band output coefficients corresponding to the blurred image are modified to replace some of the sub-band output coefficients in the set with corresponding sharp image sub-band output coefficients which correspond to edge information for the sharp image. Some of the sub-band output coefficients in the set are not replaced but are retained, and these are sub-band output coefficients which correspond to non-edge information. The resultant modified set of sub-band output coefficients can then be used in the reconstruction process.

With respect to the wavelet decomposition and reconstruction, in one embodiment, the following steps are preformed:
1. Select a modified perfect reconstruction filter bank;
2. Decompose the images into sub-bands by first filtering and down-sampling the rows of the image, then filtering and down-sampling the columns;
3. Form a set of reconstruction coefficients for the blue image including the B^LL coefficient and the band pass sub-band output coefficients corresponding to the green image (denoted by G^LH, G^HL, and G^HH) instead of using the band pass sub-band output coefficients of the blue image (denoted by B^LH, B^HL, and B^HH);
4. Depending on the degree of blur, introduce more levels of decomposition by further down-sampling and filtering the B^LL component. The green color sub-band output coefficients can replace more of the corresponding blue color sub-band output coefficients; and
5. Reconstruct by up-sampling and filtering.

More specifically, the control and processing unit 10 performs such a wavelet sub-band meshing image processing method using a modified perfect reconstruction filter bank to separate image edge information and shading information. With reference to FIG. 4, an understanding of a modified perfect reconstruction filter bank begins with an understanding of a perfect reconstruction filter bank 40. In this case, this filter bank 40 has as its input a signal denoted by B^, which represents a blurred blue image from the blue color channel after passing through a lens, where L0 represents a lens blurring function and B represents an unblurred blue image. Perfect reconstruction filter bank 40 includes a deconstruction portion 42 on the left side, a reconstruction portion 44 on the right side, and an intermediate section 43 at which sub-band output coefficients are output from the deconstruction portion 42 and input to the reconstruction portion 44.

The filter bank 40 operates to deconstruct signal B^ into a predetermined number of sub-band output coefficients corresponding to sub-bands in a wavelet domain (akin to a frequency domain) using the deconstruction portion 42. The filter bank then operates to reconstruct a version of the signal B^ using these coefficients as input to the reconstruction portion 44, with a so-called "perfect" reconstruction upon appropriate selection of filter characteristics.

As illustrated, the decomposition portion 42 of the perfect reconstruction filter bank 40 includes two cascaded levels and decomposes the input signal into four sub-bands. Specifically, at each of the two different levels, decomposition of the signal B^ occurs by filtering (using deconstruction filter H0, a low pass filter, or decomposition filter H1, a high pass filter) and downsampling (by a factor of two) to generate a respective sub-band output coefficient for each of the four different sub-bands at the intermediate section 43. For example, B^LH represents a sub-band output coefficient after filtering and down-sampling B^ twice, where L represents a low pass filter and H represents a high pass filter. The resultant sub-band output coefficients for the illustrated filter bank include B^LL, which represents the shading information, and B^LH, B^HL, and B^HH, which represent the edge information.

These sub-band output coefficients are input to the reconstruction portion 44 and up sampled (by a factor of two) and filtered (using reconstruction filters F0, a low pass filter, or reconstruction filter F1, a high pass filter) and combined, in each of two levels, to reconstruct the image signal B^. The filters H0 (low pass), F0, and H1 (high pass), F1 make up a set of perfect reconstruction filter bank pairs and appropriate selection of these filters can occur using known methods along with the constraints described below.

As shown in FIG. 5, a modified perfect reconstruction filter bank 50 also takes in image G, corresponding to a sharp image of the green color channel. This filter bank acts to at least partially decompose both blurred image B^, corresponding to the blurred image data of the blue color channel, and also image G, corresponding to the sharp image from the green color channel. Sharp image G has also passed through the lens resulting in what can be denoted G^, but because little blurring occurs, it can be assumed that G^ is approximately the same as 0. Blurred image B^ is decomposed over two levels using two low pass filters to extract its corresponding shading information in the form of a sub-band output coefficient denoted by B^LL. Further the filter bank 50 acts to at least partially decompose sharp image data G (corresponding to the sharp image data of the green color channel) to extract its corresponding edge information in the form of the sub-band output coefficients denoted by G^HL, G^LH, and G^HH. The sub-band output coefficients B^LL, G^HL, G^LH, and G^HH form a reconstruction coefficient set which is input to a reconstruction portion 54 which is the same as the reconstruction portion 44 of the perfect reconstruction filter bank 40. A new deblurred image denoted by A* is then reconstructed by using this reconstruction set by upsampling, filtering, and combining over two levels. Image A* is an improvement over blurred image B^ and maintains the shading information of the blurred blue image but has sharper edges. By using this modified filter bank 50, the color image edges can be improved without introducing false colors.

Refinements can be made by adding more cascaded levels to the reconstruction filter bank and one or more pre-filters based on the channel characteristics. As described below, a prefilter such as W0 can be added to improve results, such as to filter the image prior to decomposition. Further, the number of cascaded levels in the filter bank can be determined based on the frequency response of the initial system (filter bank and lens).

An analysis of a one-dimensional version of the system can be described with reference to FIGS. 6 and 7. Although this analysis applies to the 1-D case, these concepts can be easily extended to the 2-D case. This analysis assumes that all the filters have unit gain. FIG. 6 illustrates a 1-D standard perfect reconstruction filter bank 60, and FIG. 7 illustrates a modified prefect reconstruction filter bank 70. In both FIGS. 6 and 7, L0(z) models the blurring effects of the lens on the true blue image B(z) as a low pass filter according to: B^(z)=L0(z)B(z).

After the lens, FIG. 6 shows that a standard filter bank can be expressed as follows:

$$B\hat{}rL(z) = \frac{1}{2}F0(z)[H0(z)B\hat{}(z)+H0(-z)B\hat{}(-z)]$$

$$B\hat{}rL(z) = \frac{1}{2}F1(z)[H1(z)B\hat{}(z)+H1(-z)B\hat{}(-z)]$$

where:

B^rL is a reconstructed output in a low frequency sub-band (L) of the blurred image B^.

The filter bank of FIG. 6 is modified by replacing B^rH(z) with G^rH(z) from the green image sub-band, such as shown in FIG. 7, and expressed by:

$$G\hat{}rH(z) = \frac{1}{2}F1(z)[H1(z)G\hat{}(z)+H1(-z)G\hat{}(-z)]$$

where:

G^rH is a reconstructed output in a high frequency sub-band (H) of the image G^.

In order to reconstruct the original image data B, an estimate for the higher sub-band used in reconstruction must be close to the higher sub-band of the original B image data. From the optical properties of the lens, assume that G^ better estimates the edges of the original blue signal, as follows:

$$H1(z)G\hat{}(z)+H1(-z)G\hat{}(-z)+E_G=H1(z)B(z)+H1(-z)B(-z)$$

$$H1(z)B\hat{}(z)+H1(-z)B\hat{}(-z)+E_B=H1(z)B(z)+H1(-z)B(-z)$$

where $E_G$ represents the error in the estimate of image G, and $E_B$ represents the error in the estimate of image B.

The above two equations represent estimates of the true high pass sub-bands of B, where $E_G$ and $E_B$ are the errors of the two estimates. Because of high edge correlation, this model assumes that the absolute value of $E_G$ is less than or equal to absolute value of $E_B$.

The green color sub-band outputs are used to create a reconstructed image A*(z), where:

$$A^*(z) = B\hat{}rL(z) + G\hat{}rH(z)$$

$$= 1/2\{F0(z)[H0(z)B\hat{}(z) + H0(-z)B\hat{}(-z)]\} +$$

$$1/2\{F1(z)[H1(z)B\hat{}(z) + H1(-z)B\hat{}(-z)]\} - 1/2F1(z)E_G$$

$$= 1/2 \begin{bmatrix} F0(z)H0(z)L0(z)B(z) + F0(z)H0(-z)L0(-z)B(-z) + \\ F1(z)H1(z)B(z) + F1(z)H1(-z)B(-z) - F1(z)E_G \end{bmatrix}$$

It is desirable to remove the aliasing component B(−z) and reconstruct a delayed version of the original signal B(z). This leads to the following reconstruction conditions:

$$F0(z)H0(z)L0(z)+F1(z)H1(z)=2z\ e^{(-1)};$$

$$F0(z)H0(-z)L0(-z)+F1(z)H1(-z)=0;\text{ and}$$

$$|(F1(z)E_G)|=\epsilon$$

H0(z) and L(z) are both low pass filters. If H0(z) has a lower transition frequency than that of L0(z), then the following two approximations hold:

$H0(z)L0(z)$ is approximately equal to $H0(z)$, and $H0(-z)L0(-z)$ is approximately equal to $H0(-z)$.

These approximations simplify the three reconstruction conditions above to:

$F0(z)H0(z)+F1(z)H1(z)$ is approximately equal to $2z\ e^{(-1)}$;

$F0(z)H0(-z)+F1(z)H1(-z)$ is approximately equal to 0; and $|(F1(z)E_G)|=\epsilon$ Where the equality holds for the above three conditions, these conditions match the perfect reconstruction conditions of a conventional two-channel filter band. If the system uses a perfect reconstruction filter bank, then the output is simplified as follows:

$$A^*(z)z^{(-1)}B(z)-\frac{1}{2}F1(z)E_G$$

This process will lead to an A*(z) that closely resembles the signal B(z) with a small error factor $E_G$. $L_G$ changes spatially, and the better results will be obtained in regions where the two images have high edge correlation.

This method assumes that the lens can be modeled as a low-pass filter on the blue color channel. An analysis of the error begins with the realization that the process requires H0(z) to have a lower transition frequency than L0(z) so that the approximations set forth above are satisfied. For a two channel perfect reconstruction filter bank, H0 has a transition band centered at ω=0.5 π. If it is determined that the L0(z) transition frequency of the lens is less than 0.5 π, then additional levels of sub-band decomposition can be added to the filter bank 50.

The above analysis suggests that there is a trade-off between the error created by using the green sub-band outputs and the error created by the lens when blurring the blue sub-bands. Rather than recovery of the high frequencies, the deblurring method replaces this part of the spectrum with the corresponding green sub-band output coefficients, although when the low-pass lens filter no longer passes the higher frequency sub-bands, then the trade-off favors using the green sub-bands. The levels of decomposition, c, can be increased until the transition frequency of the blurring filter falls beyond the transition frequency of the lowest sub-band.

Determining the levels of decompositions involves the following considerations. Recall that $L0(e^{j\omega})$ represents the blur filter of the blue image. An appropriate frequency response is as follows: $L0(e^{j\omega})$ is approximately 1 if $|\omega|<\pi 4$, and is approximately 0 if $\pi/4 \leq |\omega| < \pi$.

Thus, the method should use the blue sub-bands for all frequencies $|\omega|<\pi/4$ that the lens passes, and use the green sub-bands for all frequencies $\pi/4 \leq |\omega| < \pi$. For this $L0(e^{j\omega})$, the method requires a two level decomposition, such as shown in FIGS. 5 and 7. Further:

$$B\hat{}LL(z) = 1/2[H0(z^{1/2})1/2(H0(z^{1/4})B\hat{}(z^{1/4}) + (H0(-z^{1/4})B\hat{}(-z^{1/4})))] +$$

$$1/2[H0(-z^{1/2})1/2(H0(jz^{1/4})B\hat{}(jz^{1/4}) + (H0(-jz^{1/4})B\hat{}(-jz^{1/4})))]$$

Instead of using the B^LH, B^HL, and B^HH terms, this method uses instead the respective G^LH, G^HL, and G^HH terms. The B^LH, B^L, and B^HH sub-band terms estimate the original B image poorly. The unfiltered sub-bands terms of G^LH, G^HL, and G^HH estimate the B signal well because of strong edge correlation. The reconstruction error depends on the accuracy of the estimate of these sub-band terms.

Now consider the following change of variables:

$$R(z)=H0(z)[B(z)-B\hat{}(z)], \text{ and}$$

$$P(z)=H0(z)B(z)(1-L0(z)).$$

$E_{BLL}$ (z) represents the error between BLL and B^LL, and can be expressed as follows:

$$\begin{aligned}E_{BLL}(z) &= BLL(z) - B\wedge LL(z)\\ &= 1/4[H0(z^{1/2})R(z^{1/4})] + 1/4[H0(z^{1/2})R(-z^{1/4})] +\\ &\quad 1/4[H0(-z^{1/2})R(jz^{1/4})] + 1/4[H0(-z^{1/2})R(-jz^{1/4})]\\ &= 1/4[H0(z^{1/2})P(z^{1/4})] + 1/4[H0(z^{1/2})P(-z^{1/4})] +\\ &\quad 1/4[H0(-z^{1/2})P(jz^{1/4})] + 1/4[H0(-z^{1/2})P(-jz^{1/4})]\end{aligned}$$

Thus, four distinct terms comprise $E_{BLL}(z)$. For the first term, $L0(e^{j\omega/4})$ is approximately 1 when $|\omega|$ is less than $\pi$, thus the first term is approximately 0. For the second term, H0 is a low-pass filter. Thus $H0(-e^{j\omega/4})$ is approximately equal to zero by construction and the second term is approximately 0. For the remaining two terms, $H0(-e^{j\omega/2})$ is approximately 0 and those terms are approximately 0. In order to make $E_{BLL}(z)$ small, H0 should approximate an ideal low-pass filter as much as possible. This effect suggests that adding more coefficients to the filters will improve performance. Because $L0(e^{j\omega/4})$ passes the frequencies in this sub-band, the estimate produces a small error $E_{BLL}(z)$.

Consider generalizing L0, such that $L0(e^{j\omega})$ is approximately 1 if $|\omega|$ less than $\omega_0$, and is approximately 0 if $|\omega|$ is greater than or equal to $\omega_0$ and less than $\pi$.

In order to reduce the overall error, the decomposition level c can increase until $\pi/2^c$ is less than or equal to $\omega_0$, and $\omega_0$ is less than or equal to $\pi/2^{c-1}$. Choosing a large c means discarding parts of the frequency spectrum which the lens does not actually corrupt. Making c too small will increase the error because in the low band of the frequency spectra 0 is not equal to (1-L(z)).

In other words, the optical properties of the lens blur out B^LH, B^HL, and B^HH and yield a high approximation error. G^LH, G^HL and G^HH better estimate the edges of the original blue signal.

$$E_{BLH}=BLH-B\hat{}LH$$

$$E_{BHL}=BHL-B\hat{}HL$$

$$E_{BHH}=BHH-B\hat{}HH$$

$$E_{GLH}=GLH-G\hat{}LH$$

$$E_{GHL}=GHL-G\hat{}HL$$

$$E_{GHH}=GHH-G\hat{}HH$$

Here $|E_{GHH}| \leq |E_{BHH}|; |E_{GHL}| \leq |E_{BHL}|;$ and $|E_{GHL}| \leq |E_{BLH}|$.

Recall that G^LH, G^HL and G^HH then pass through the reconstruction portion of the filter bank. Thus, the filter band must satisfy known reconstruction conditions such as set forth in G. Strang and T. Q. Nguyen, "Wavelets and filter banks", Cambridge, Mass.: Wellesley-Cambridge, 1997, which is hereby incorporated by reference herein. The following expresses the output of the filter bank:

$$A^*(z)=z^{-1}B(z)-F0(z)F0(z^2)E_{BLL}-F0(z)F1(z^2)E_{GLH}-F1(z)F0(z^2)E_{GHL}-F1(z)F1(z^2)E_{GHH}$$

Increasing the decomposition level c causes more $E_G$ terms to appear. To reduce $E_{BLL}$ without introducing extra $E_G$ terms, level c should be increased until $\pi/2^c \leq \omega_0 \leq \pi 2^{c-1}$.

Best results are obtained by limiting the number of $E_G$ terms, and using only the sub-bands with small $E_B$ terms. Similar to above, consider the error $E_{BLH}$ between BLH and B^LH:

$$\begin{aligned}E_{BLH}(z) &= BLH(z) - B\wedge LH(z)\\ &= 1/4[H1(z^{1/2})P(z^{1/4})] + 1/4[H1(z^{1/2})P(-z^{1/4})] +\\ &\quad 1/4[H1(-z^{1/2})P(jz^{1/4})] + 1/4[H1(-z^{1/2})P(-jz^{1/4})]\end{aligned}$$

Again, this expression includes four terms. The first three terms are approximately zero by construction because $H1(e^{j\omega/2})$ is approximately zero and $H0(e^{j\omega/4})$ is approximately zero. However, the last term contains error. To reduce this error, G^LH can replace B^LH as discussed above. For the lower frequency sub-bands, the correlation does poorly and the reconstruction suffers.

To reduce the error further, a pre-filter $W0(z)$ can be added directly after $L0(z)$ in FIG. 5. By adding this filter, the fourth term of the prior equation changes to:

$$\tfrac{1}{4}Q(-jz^{1/4})[1-L0(-jz^{1/4})W0(jz^{1/4})]$$

where $Q(z)=H1(z^2)H0(z^2)H0(z)B(z)$.

To make the last term approximately zero, the filter $W0(z)$ needs to satisfy the following:

$$1-L0(-jz^{1/4})W0(-jz^{1/4})=0$$

Assume more is known about $L0(e^{j\omega})$, as for example that $L0(e^{j\omega})$ is approximately:

1 if $|\omega|<\omega_0$; $\delta$ if $\omega_0<|\omega|<\omega_\delta$; and 0 if $\omega_\delta<|\omega|<\pi$.

Here $0<\delta<1$ represents the transition band. The first zero of $L0(e^{j\omega})$ has a higher frequency than $\omega_\delta$. A modified Wiener filter can be designed to reduce the error in all sub-bands with frequencies below $\omega_\delta$. The filter bank design increases the level of decomposition so that the highest B^ sub-band used in reconstruction has a transition frequency that is arbitrarily close to $\omega_\delta$. In practice, complexity and image size limit the number of levels of decomposition.

In another embodiment, a contourlet sub-band meshing method is used for deblurring an image in a first color channel, such as a blue (or red) channel, using information from a second sharp color channel, such as a green channel. This method is similar to the wavelet-based meshing method described above in that decomposition and reconstruction are involved. However, the contourlet sub-band meshing method uses a contourlet transform instead of a wavelet transform and generates an edge map for further analysis of the edges prior to substitution of some green coefficients for blue ones in the reconstruction of the deblurred blue image.

The contourlet transform was recently proposed by Do and Vetterli as a directional multi-resolution image representation that can efficiently capture and represent smooth object boundaries in natural images (as discussed in Minh N. Do and Martin Vetterli, "The contourlet transform: An efficient directional multi resolution image representation," IEEE Trans. on Image Processing, vol. 18, pp. 729-739, April 2009, which is hereby incorporated by reference herein). More specifically, the contourlet transform is constructed as an iterated double filter bank including a Laplacian pyramid stage and a directional filter bank stage. Conceptually, the operation can be illustrated with reference to FIGS. 8a-8b. A Laplacian pyramid iteratively decomposes a 2-D image into low pass and high pass sub-bands, and directional filter banks are applied to the high pass sub-bands to further decompose the frequency spectrum. The process is iteratively repeated using a downsampled version of the low pass output as input to the next stages. Using ideal filters, the contourlet transform will decompose the 2-D frequency spectrum into trapezoid-shaped sub-band regions as shown in FIG. 8b.

A two dimensional decomposition portion 90 of a contourlet filter bank is schematically shown in FIG. 9, and is operationally somewhat similar to the operation of the decomposition portion of the filter banks described above. Using this two level contourlet decomposition filter bank for the blue channel, a decomposition of the blue image produces three outputs: the low pass output B^LL, the band pass output B^LH, and the high pass output B^HH. The green image is similarly decomposed to generate G^LH and G^HH, which can be substituted for the B^LH and B^HH coefficients as described below. Of course more levels or stages of iteration can be added to decompose the image into many more sub-bands. The blue image and the green image are both decomposed using a desired number of levels or stages.

An ant colony optimization edge detection scheme of this method produces a binary edge map which is then dilated and used to decide which sub-band output coefficients corresponding to the blue channel will be replaced with green sub-band output coefficients and which sub-bands output coefficients will not be replaced. Improved results compared to conventional methods can be obtained because the variable nature of contourlets allows for the natural contours of an image to be more accurately defined. Further, the edge detection scheme allows for the characterization of edges as strong or weak.

Consequently, the contourlet sub-meshing method can be performed as follows:

1. Select a contourlet filter bank and decompose both the green and the blue image into sub-hands by filtering and down-sampling, to generate corresponding sub-band output coefficients for each image.

2. Detect major edges in the green color channel based on an ant colony optimization (ACO) edge detection scheme to create a binary map in the contourlet domain. The binary edge map can be dilated to collect the area around detected major edges such that areas around the edges in the contourlet domain will also take a value of 1 rather than 0.

3. Select each coefficient of the band-pass contourlet sub-bands according to the dilated binary edge map, which is used to determine the best coefficient (green or blue).

4. Depending on the degree of blur, additional levels of decomposition can be introduced by further down-sampling and filtering the lowest frequency sub-band. The green color sub-bands can then replace more of the corresponding blue color sub-bands. The lowest sub-band should remain the original blurred blue color sub-band in order to reduce false coloring.

5. Reconstruct the blue image by up-sampling, filtering, and combining as appropriate.

Further with respect to the ACO edge detection scheme, this scheme is described in an article by Jing Tian; Weiyu Yu, and Shengli Xie, titled "An ant colony optimization algorithm for image edge detection," in IEEE Congress on Evolutionary Computation, 2008, pages 751-756, which is hereby incorporated by reference herein. The ACO scheme arises from the natural behavior of ants in making and following trails. Here, a binary edge map for the green channel can be generated with each sub-band having a value of 1 or 0 depending on whether a strong edge is present or not. Dilation allows more of the green coefficients to be used. Let $g_{em}$ be the dilated green edge map in the contourlet domain. Then, a new coefficient for a sub-band is generated based on this map, for example:

$$ALH(w) = B^\wedge LH(\omega) \text{ if } g_{em}(\omega) = 0$$
$$= G^\wedge LH(\omega) \text{ if } g_{em}(\omega) = 1$$

Thus this method replaces some of the blurred blue edges with sharp green edges but keeps those blurred blue edges which correspond to weak green edges. This method assumes that a strong green edge indicates a similarly strong true blue edge and chooses a corresponding green coefficient. In areas with a, weak green edge, the method assumes that the blurred blue edge better matches the true sharp blue image and chooses the corresponding blue coefficient. Natural images usually adhere to this generalization and thus improved image reconstruction can be achieved.

An appropriate dilation radius (such as in the range of 5-25 pixels) is selected. At a higher dilation radius, the border around the edges increases and fewer ghosting artifacts occur. Also, at a higher dilation radius, the edges will appear sharper, but the shading will differ from the clean image.

More particularly, mixing coefficients between the two color channels creates ghosting artifacts. The mean squared error (MSE) between the reconstructed image and the original image becomes a function of these artifacts:

$$\text{MSE}_{BB} = F(A_{ghost}(g_{em}), G_{edge}(g_{em}))$$

A trade off exists because the green coefficients produce sharp edges, but can result in false coloring. Mixing with blue coefficients produces less false coloring, but introduces ghosting artifacts. The goal is to minimize this trade-off and produce a natural looking image.

Consider B^LH expressed in terms of B(w1, w2). As illustrated in FIG. 10a, the band-pass output can be expressed as shown, where HL is a low pass filter, HH is a high-pass filter, and HD is a group of directional filters. Only the term when m=0, n=0 matters, as all the other terms are close to 0. The clean blue image and green image have similar BLH and G^LH terms. Thus, the method uses GLH when it has a smaller MSE as expressed in FIG. 10b. Many of the similar terms can combined into variable a, as shown in FIG. 10c, which can then be simplified as shown in FIG. 10d. The difference of squares then results in the inequality shown in FIG. 10e, which leads to the two conditions shown in FIG. 10f. If either of these conditions is satisfied, then a better MSE is achieved. By construction, L0($\omega$1/2, $\omega$2/2) B($\omega$1/2, $\omega$2/2) =B^($\omega$1/2, $\omega$2/2) is the blurred blue image obtained from the camera. The last two conditions of FIG. 10f can be rewritten as shown in FIG. 10g.

Similar conditions can be produced for each of the outputs of the deconstruction filter bank. In the high frequency sub-bands, L0($\omega$1/2, $\omega$2/2) is approximately zero and blurs out these coefficients. Under these circumstances, the expression shown in FIG. 10f becomes:

$$0 < \frac{G^\wedge(\omega_1/2 - \omega_2/2)}{B(\omega_1/2 - \omega_2/2)} < 2$$

For the high frequency components, the numerator and the denominator of the expression above will typically have similar magnitude, satisfying the upper bound. The expression above also suggests that in the high frequency sub-bands, the method will reduce the MSE when the green and clean blue coefficients have the same sign and a strong correlation exists between the color channels. In areas where they have different signs, the condition fails, and the poor correlation with result in color bleeding.

For the lowest frequency components, the blur kernel (L0) does not affect these frequencies, and thus $L0(\omega 1/2, \omega 2/2)$ is approximately 1. In this case, $B(\omega 1/2, \omega 2/2)$ is approximately equal to $B^\wedge(\omega 1/2, \omega 2/2)$, and the equations of FIG. 10g are not satisfied. Intuitively, the blur kernel does not affect the lower frequencies and substituting in green sub-bands at these lower frequencies does not reduce the MSE.

The contourlet method is an improvement over the wavelet method. Further, as the size of the blur kernel increases, the input image quality decreases and the PSNR (Peak Signal to Noise Ratio) decreases. With the blue image more degraded, more of the green color channel coefficients can be used. This means that more levels of decomposition are required.

The camera system 2 has been described with respect to its use in imaging body cavities as can be employed in MIS. However, other applications for the camera system and color correction algorithm are also contemplated. For example, cameras with extensive zoom control are available today for use in outer space for homeland security purposes. Light sources for enable the use of such cameras remains an issue in conventional designs. Either the distance or the desire to remain unrecognized prevents the use of a light source directly from the location of the camera. A camera system such as described herein including light source assemblies and network communications can resolve this difficulty. A powerful camera can be positioned miles away from the target sites as long as the light source is able to adjust itself according to the movement of the camera. Wireless communication between the light source assemblies and the camera can enable the use of the camera even when very distant from the target, for example, when airborne and mobile. Embodiments of the present invention can also enable various systems that use only one powerful camera that is centrally located with the ability to acquire images from different areas, as long as it includes a light source for each area of interest.

Also for example, embodiments of the present invention are also suitable for various civilian purposes such as using a powerful light source with variable illumination pattern and steering capability among different groups. Having a powerful light source that can be used by different consumers will allow landing airplanes and docking ships to use the light source of the airport or the seaport for assistance in landing. This will enable the consumers to direct the light to where it is needed rather than have a standard stationary illumination. Further for example, a system such as the camera system 2 can be used for imaging other spaces and regions other than cavities of the human body (or cavities in an animal body), including spaces or regions that are otherwise hard to reach.

Additionally, while much of the above description relates to the camera system 2, which has both the camera 4 as well as one or more of the light source assemblies 6, 8 (as well as the control and processing unit 10), the present invention is also intended to encompass other applications or embodiments in which only one or more of these components is present. For example, the present invention is also intended to relate to a light source assembly that is independent of any camera and merely used to provide lighting for a desired target. That is, the present invention is also intended to encompass, for example, a stand-alone light source assembly such as that described above that employs (i) one or more tunable lenses for the purpose of controlling an output light pattern (e.g., amount of light divergence), and/or (ii) controllable LEDs that can be switched on and off to cause variations in light beam direction.

Any system with high edge correlation can benefit from the above-described deblurring algorithm. Other future applications include uses in super resolution and video compression. For super resolution, all three color planes share the same edge information, the resulting color image has much sharper edges than traditional techniques. For video compression, the edge information is redundant between color planes, such that one can use the edge information from one color plane as edge information for all three color planes. This redundancy can be used to save on the number of bits required without sacrificing much in terms of quality. Another example is in systems where one sharp image sensor can improve the quality of an inexpensive sensor such as infrared which has high edge information. Using the same concept of wireless network and motion estimation but instead of having a light source having a powerful weapon will enable land forces to be mobile and use a heavy weapon at the same time. This weapon could be located far from the fire zone or even airborne and could be used by multiple consumers. The weapon can be locked into target by a camera carried by the consumer as long as its spatial orientation is registered and communication to the weapon is available. Motion estimation and distance to the target can be calculated in the processor near the weapon.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method for deblurring a blurred first image corresponding to a first color channel of a camera that also produces a sharp second image corresponding to a second color channel of the camera, wherein the first and the second images each include a plurality of pixels with each pixel having an associated respective value, the method comprising:

decomposing the first image by filtering and downsampling to generate a first set of one or more first sub-band output coefficients, wherein each first sub-band output coefficient corresponds to a respective sub-band in a selected one of a wavelet and a contourlet domain;

decomposing the second image by filtering and downsampling to generate a second set of second sub-band output coefficients, wherein each second sub-band output coefficient corresponds to a respective sub-band in the selected domain;

selecting those second sub-band output coefficients that represent edge information, each of the selected second sub-band output coefficients corresponding to a respective selected sub-band, with the selected sub-bands together defining an edge sub-band set;

preparing a third set of sub-band output coefficients which includes the selected second sub-band output coefficients representing edge information and at least one of the first sub-band output coefficients corresponding to a sub-band other than those sub-bands in the edge sub-band set; and reconstructing a deblurred first image by upsampling and filtering using the third set of sub-band output coefficients as input.

2. The method of claim 1, wherein each decomposing step occurs over two or more levels and the reconstructing step occurs over the same number of levels.

3. The method of claim 2, wherein the number of levels of decomposition is determined based at least in part on a frequency response of a blurring lens of the camera.

4. The method of claim 1, the first set and the second set are combined to form the third set.

5. The method of claim 1, wherein the sub-bands corresponding to first set and the second set are predetermined and non-overlapping.

6. The method of claim 1, further including prefiltering the second image prior to decomposition of the second image.

7. The method of claim 6, wherein the prefiltering uses a Wiener filter.

8. The method of claim 1, wherein the decomposition steps occur in the contourlet domain and the selected second sub-band output coefficients are those which have been determined to represent edge information.

9. The method of claim 8, wherein the edge information is determined using an ant colonization optimization scheme.

10. A method for deblurring a first image of a camera, wherein the camera generates the first image corresponding to a first color channel and a second image corresponding to a second color channel, wherein the first and the second images each includes a plurality of pixels with each pixel having an associated respective value, the method comprising:

selecting a filter bank having a decomposition portion and a reconstruction portion, the decomposition portion having at least two cascaded levels for receiving two inputs and generating intermediate sub-band output coefficients for each of a predetermined number N of sub-bands, the reconstruction portion having at least two cascaded levels for receiving the intermediate sub-band output coefficients and generating an output, wherein the decomposition portion includes multiple decomposition stages at a first level connecting to N decomposition stages at a second level, each decomposition stage including at least one of a decomposition filter and a downsampler, wherein the reconstruction portion includes N reconstruction stages at a third level connecting to N/2 reconstruction stages at a fourth level, each reconstruction stage including at least one of an upsampler and a reconstruction filter;

decomposing the first image using a first part of the decomposition portion of the filter bank to generate at least one first intermediate sub-band output coefficient corresponding to one of the N sub-bands;

decomposing the second image using a second part of the decomposition portion of the filter bank to generate at least a second, a third intermediate, and a fourth sub-band output coefficient, each corresponding to a respective one of the N sub-bands; and reconstructing a deblurred image corresponding to the first color channel using at least the first, the second, the third, and the fourth sub-band output coefficients as input to the reconstruction side of the filter bank, wherein each decomposing step occurs over two or more levels and the reconstructing step occurs over the same number of levels and the number of levels of decomposition is determined based at least in part on a frequency response of a blurring lens of the camera.

11. The method of claim 10, wherein the sub-bands corresponding to intermediate sub-band output coefficients of the first image are non-overlapping with the sub-bands corresponding to the intermediate sub-band output coefficients of the second image.

12. The method of claim 10, further including prefiltering the second image prior to decomposition of the second color image.

13. The method of claim 12, wherein the prefiltering uses a Wiener filter.

14. A method for deblurring a blurred first image, wherein the blurred first image corresponds to a first color channel of a camera and a second image corresponds to a second color channel of the camera, wherein the first and the second images each comprise a plurality of pixels with each pixel having an associated respective value, the method comprising:

decomposing the first image by filtering and downsampling in a decomposition portion of a filter bank to generate for a predetermined number of sub-bands in a contourlet domain a first set of first sub-band output coefficients, wherein each first sub-band output coefficient corresponds to a respective one of the sub-bands;

decomposing the second image by filtering and downsampling in the decomposition portion of the filter bank to generate for the predetermined number of sub-bands a second set of second sub-band output coefficients, wherein each second sub-band output coefficient corresponds to a respective one of the sub-bands in the contourlet domain;

determining which of the second sub-band output coefficients and corresponding respective sub-bands represent edge information;

preparing a set of third sub-band output coefficients by modifying the first set of first sub-band output coefficients to replace each of those first sub-band output coefficients in the first set which correspond to the respective determined sub-bands representing edge information with the corresponding second sub-band output coefficients from the second set; and reconstructing a deblurred image corresponding to the first image by upsampling and filtering the set of third sub-band output coefficients in a reconstruction portion of the filter bank.

15. The method of claim 14, further including combining the deblurred image with the second image to generate a composite color image.

16. The method of claim 14, wherein the edge information is determined using an ant colonization optimization scheme.

17. The method of claim 16, further including preparing a binary edge map in the contourlet domain and using the binary edge map in the preparing step to select corresponding second sub-band output coefficients from the second set.

18. The method of claim 17, further including preparing a binary edge map in the contourlet domain, dilating the binary edge map, and using the dilated binary edge map in the preparing step to select corresponding second sub-band output coefficients from the second set.

19. A method for deblurring a blurred first image corresponding to a first color channel of a camera that also produces a sharp second image corresponding to a second color channel of the camera, wherein the first and the second images each include a plurality of pixels with each pixel having an associated respective value, the method comprising:

decomposing the first image by filtering and downsampling to generate a first set of one or more first sub-band output coefficients, wherein each first sub-band output coefficient corresponds to a respective sub-band in a selected one of a wavelet and a contourlet domain;

decomposing the second image by filtering and downsampling to generate a second set of second sub-band output coefficients, wherein each second sub-band output coefficient corresponds to a respective sub-band in the selected domain;

selecting those second sub-band output coefficients that represent edge information, each of the selected second sub-band output coefficients corresponding to a respective selected sub-band, with the selected sub-bands together defining an edge sub-band set;

preparing a third set of sub-band output coefficients which includes the selected second sub-band output coefficients representing edge information and at least one first sub-band output coefficient corresponding to a sub-band other than those sub-bands in the edge sub-band set; and reconstructing a deblurred first image by upsampling and filtering using the third set of sub-band output coefficients as input, wherein each decomposing step occurs over two or more levels and the reconstructing step occurs over the same number of levels, and wherein the number of levels of decomposition is determined based at least in part on a frequency response of a blurring lens of the camera.

20. A method for deblurring a blurred first image, wherein the blurred first image corresponds to a first color channel of a camera and a second image corresponds to a second color channel of the camera, wherein the first and the second images each comprise a plurality of pixels with each pixel having an associated respective value, the method comprising:

decomposing the first image by filtering and downsampling in a decomposition portion of a filter bank to generate for a predetermined number of sub-bands in a contourlet domain a first set of first sub-band output coefficients, wherein each first sub-band output coefficient corresponds to a respective one of the sub-bands;

decomposing the second image by filtering and downsampling in the decomposition portion of the filter bank to generate for the predetermined number of sub-bands a second set of second sub-band output coefficients, wherein each second sub-band output coefficient corresponds to a respective one of the sub-bands in the contourlet domain;

determining which of the second sub-band output coefficients and corresponding respective sub-bands represent edge information, wherein the edge information is determined using an ant colonization optimization scheme;

preparing a set of third sub-band output coefficients by modifying the first set of first sub-band output coefficients to replace each of those first sub-band output coefficients in the first set which correspond to the respective determined sub-bands representing edge information with the corresponding second sub-band output coefficients from the second set; and reconstructing a deblurred image corresponding to the first image by upsampling and filtering the set of third sub-band output coefficients in a reconstruction portion of the filter bank, wherein the method further includes:

preparing a binary edge map in the contourlet domain and using the binary edge map in the preparing step to select corresponding second sub-band output coefficients from the second set; and preparing a binary edge map in the contourlet domain, dilating the binary edge map, and using the dilated binary edge map in the preparing step to select corresponding second sub-band output coefficients from the second set.

* * * * *